(12) United States Patent
Ziemek et al.

(10) Patent No.: US 12,295,620 B2
(45) Date of Patent: May 13, 2025

(54) BONE SCREW THREADED ENLARGER

(71) Applicant: Zimmer Biomet Spine, Inc., Westminster, CO (US)

(72) Inventors: Terry Ziemek, Broomfield, CO (US); David W. Castleman, Minneapolis, MN (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 18/332,617

(22) Filed: Jun. 9, 2023

(65) Prior Publication Data
US 2023/0320761 A1 Oct. 12, 2023

Related U.S. Application Data

(62) Division of application No. 17/062,138, filed on Oct. 2, 2020, now Pat. No. 11,707,300, which is a division
(Continued)

(51) Int. Cl.
*A61B 17/70* (2006.01)
*A61B 17/86* (2006.01)
(Continued)

(52) U.S. Cl.
CPC ...... *A61B 17/7032* (2013.01); *A61B 17/7035* (2013.01); *A61B 17/8605* (2013.01);
(Continued)

(58) Field of Classification Search
CPC ............ A61B 17/7032; A61B 17/7035; A61B 17/8605; A61B 17/8685
See application file for complete search history.

(56) References Cited

U.S. PATENT DOCUMENTS 4,711,232 A 12/1987 Fischer et al.
7,951,173 B2 5/2011 Hammill, Sr. et al.
(Continued)

FOREIGN PATENT DOCUMENTS

GB 2512063 9/2014
WO WO 2010/111470 9/2010
(Continued)

OTHER PUBLICATIONS

Decision to Grant for European Patent Application No. 17749087.7, dated Sep. 28, 2023 2 pages.
(Continued)

*Primary Examiner* — Olivia C Chang
(74) *Attorney, Agent, or Firm* — Sheridan Ross P.C.

(57) ABSTRACT

A bone fastener system can comprise a fastener and a first sizing component. The fastener can comprise a shaft that provides an anchoring footprint. The first sizing component can be configured to be connected to the shaft and can include a first anchoring feature, or circumferential bone engaging feature, to increase a size of the anchoring footprint. The first anchoring feature can comprise a sleeve that radially expands a diameter of the threaded shaft. The first anchoring feature can comprise axially extending teeth. The system can further comprise a second sizing component including a second anchoring feature to increase the size of the anchoring footprint, the second anchoring feature being different from the first anchoring feature. The second anchoring feature can expand the diameter of the threaded shaft a greater amount than the first anchoring feature. The second anchoring feature can have a length greater than the first anchoring feature.

19 Claims, 7 Drawing Sheets

Related U.S. Application Data of application No. 15/663,174, filed on Jul. 28, 2017, now Pat. No. 10,820,928.

(60) Provisional application No. 62/482,136, filed on Apr. 5, 2017, provisional application No. 62/368,345, filed on Jul. 29, 2016.

(51) Int. Cl.
    *A61B 17/56*     (2006.01)
    *A61B 90/00*     (2016.01)

(52) U.S. Cl.
CPC ........ *A61B 17/863* (2013.01); *A61B 17/8635* (2013.01); *A61B 17/8685* (2013.01); *A61B 17/8695* (2013.01); *A61B 2017/564* (2013.01); *A61B 17/7037* (2013.01); *A61B 2017/8655* (2013.01); *A61B 2017/867* (2013.01); *A61B 2090/061* (2016.02)

(56) References Cited

U.S. PATENT DOCUMENTS

| | | | |
|---|---|---|---|
| 8,162,998 | B2 | 4/2012 | Schlienger et al. |
| 8,163,031 | B2 | 4/2012 | Truckai et al. |
| 8,221,479 | B2 | 7/2012 | Glazer et al. |
| 8,343,200 | B2 | 1/2013 | Khanna et al. |
| 8,496,685 | B2 | 7/2013 | Landry et al. |
| 8,512,382 | B2 | 8/2013 | Cawley et al. |
| 8,961,568 | B2 | 2/2015 | McKinley et al. |
| 9,161,794 | B2 | 10/2015 | Garvey |
| 9,216,043 | B2 | 12/2015 | Stad et al. |
| 9,289,244 | B2 | 3/2016 | Hestad et al. |
| 10,820,928 | B2 | 11/2020 | Ziemnek et al. |
| 10,828,070 | B2 | 11/2020 | Ziemek et al. |
| 11,707,300 | B2 | 7/2023 | Ziemek et al. |
| 2004/0210227 | A1 | 10/2004 | Trail et al. |
| 2005/0273101 | A1 | 12/2005 | Schumacher |
| 2006/0217717 | A1 | 9/2006 | Whipple |
| 2008/0086131 | A1 | 4/2008 | Daly et al. |
| 2010/0057135 | A1 | 3/2010 | Heiges et al. |
| 2010/0137920 | A1 | 6/2010 | Hammill, Sr. et al. |
| 2011/0105172 | A1 | 5/2011 | Wallenstein et al. |
| 2011/0190821 | A1* | 8/2011 | Chin ................ A61B 17/864 606/264 |
| 2012/0029566 | A1 | 2/2012 | Rezach |
| 2012/0143262 | A1 | 6/2012 | Jensen et al. |
| 2013/0018427 | A1 | 1/2013 | Pham et al. |
| 2013/0338715 | A1* | 12/2013 | Daly ................ A61B 17/7053 606/279 |
| 2015/0100096 | A1 | 4/2015 | Protopsaltis et al. |
| 2016/0143667 | A1* | 5/2016 | Beger ............... A61B 17/7044 606/272 |
| 2016/0287301 | A1 | 10/2016 | Mehl et al. |
| 2018/0028246 | A1 | 2/2018 | Kang et al. |
| 2018/0055542 | A1 | 3/2018 | Biedermann |
| 2018/0153588 | A1 | 6/2018 | Mosnier et al. |
| 2021/0022772 | A1 | 1/2021 | Ziemek et al. |

FOREIGN PATENT DOCUMENTS

| | | |
|---|---|---|
| WO | WO 2011/056707 | 5/2011 |
| WO | WO 2017/035186 | 3/2017 |
| WO | WO 2018/023030 | 2/2018 |
| WO | WO 2018/023034 | 2/2018 |

OTHER PUBLICATIONS

Notice of Allowance for U.S. Appl. No. 17/062,184, dated Sep. 20, 2023 6 pages.
"International Application Serial No. PCT/US2017/044435, International Search Report mailed Oct. 30, 2017", 4 pages.
"International Application Serial No. PCT/US2017/044435, Written Opinion mailed Oct. 30, 2017", 7 pages.
"International Application Serial No. PCT/US2017/044435, International Preliminary Report on Patentability mailed Feb. 7, 1929", 9 pages.
"International Application Serial No. PCT/US2017/044440, International Search Report mailed Oct. 30, 2017", 4 pages.
"International Application Serial No. PCT/US2017/044440, Written Opinion mailed Oct. 30, 2017", 6 pages.
"International Application Serial No. PCT/US2017/044440, International Preliminary Report on Patentability mailed Feb. 7, 2019", 8 pages.
"European Application Serial No. 17749326.9, Communication Pursuant to Article 94(3) EPC mailed Nov. 22, 2019", 5 pages.
"European Application Serial No. 17749326.9, Response to Communication pursuant to Rules 161(1) and 162 EPC filed Sep. 23, 2019", 18 pages.
"European Application Serial No. 17749326.9, Response filed Apr. 2, 2020 to Communication Pursuant to Article 94(3) EPC mailed Nov. 22, 2019", 13 pages.
"European Application Serial No. 17749087.7, Response to Communication pursuant to Rules 161(1) and 162 EPC filed Sep. 20, 2019", 26 pages.
Official Action for European Patent Application No. 17749087.7, dated Aug. 10, 2022 6 pages.
Official Action for U.S. Appl. No. 15/663,174, dated Aug. 2, 2019 8 pages, Restriction Requirement.
Official Action for U.S. Appl. No. 15/663,174, dated Oct. 16, 2019 6 pages.
Final Action for U.S. Appl. No. 15/663,174, dated Mar. 20, 2020 8 pages.
Notice of Allowance for U.S. Appl. No. 15/663,174, dated Jul. 1, 2020 7 pages.
"U.S. Appl. No. 15/663,174, Response filed Jan. 15, 2020 to Non Final Office Action mailed Oct. 16, 2019", 13 pages.
"U.S. Appl. No. 15/663,174, Response filed Jun. 19, 2020 to Final Office Action mailed Mar. 20, 2020", 14 pages.
"U.S. Appl. No. 15/663,174, Response filed Oct. 2, 2019 to Restriction Requirement mailed Aug. 2, 2019", 8 pages.
Official Action for U.S. Appl. No. 17/062,138, dated Apr. 15, 2022 7 pages, Restriction Requirement.
Official Action for U.S. Appl. No. 17/062,138, dated Oct. 25, 2022 8 pages.
Notice of Allowance for U.S. Appl. No. 17/062,138, dated Mar. 9, 2023 7 pages.
Official Action for U.S. Appl. No. 17/062,184, dated Apr. 15, 2022 6 pages, Restriction Requirement.
Official Action for U.S. Appl. No. 17/062,184, dated Jul. 20, 2022 8 pages.
Final Action for U.S. Appl. No. 17/062,184, dated Dec. 28, 2022 8 pages.
Notice of Allowance for U.S. Appl. No. 17/062,184, dated Feb. 27, 2023 8 pages.
"U.S. Appl. No. 15/663,188, Restriction Requirement mailed Jul. 22, 2019", 6 pages.
"U.S. Appl. No. 15/663,188, Non Final Office Action mailed Oct. 11, 2019", 7 pages.
"U.S. Appl. No. 15/663,188, Final Office Action mailed Mar. 20, 2020", 9 pages.
"U.S. Appl. No. 15/663,188, Notice of Allowance mailed Jul. 7, 2020", 7 pages.
"U.S. Appl. No. 15/663,188, Response filed Sep. 23, 2019 to Restriction Requirement mailed Jul. 2022, 19", 14 pages.
"U.S. Appl. No. 15/663,188, Response filed Jan. 13, 2020 to Non Final Office Action mailed Oct. 11, 2019", 22 pages.
"U.S. Appl. No. 15/663,188, Response filed Jun. 19, 2020 to Final Office Action mailed Mar. 20, 2020", 15 pages.
Extended Search Report for European Patent Application No. 23199942.6, dated Jan. 23, 2024 10 pages.

* cited by examiner

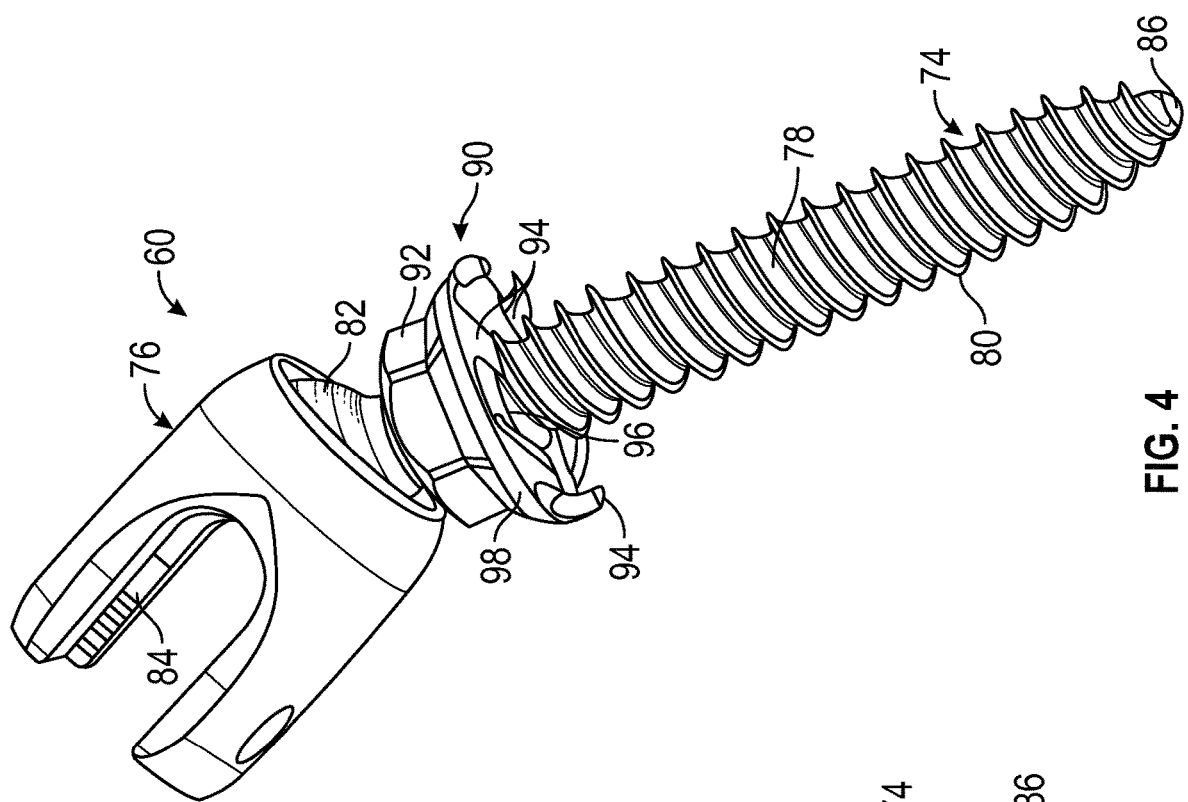
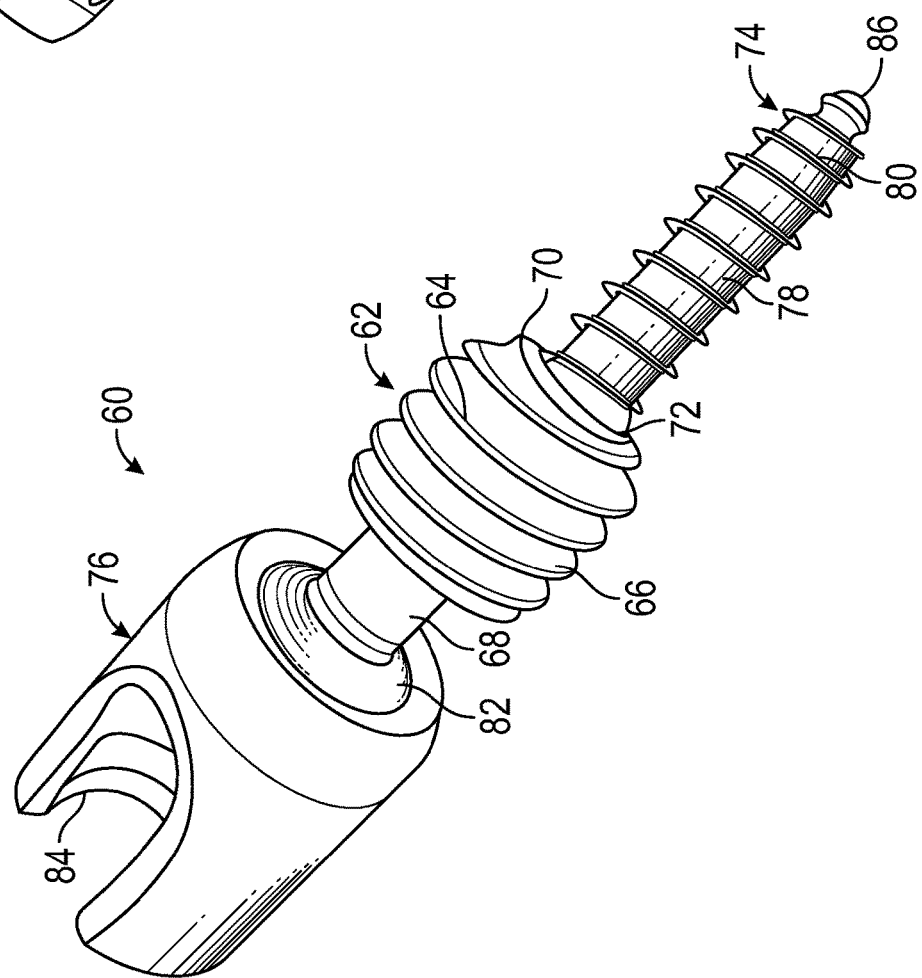

BONE SCREW THREADED ENLARGER

CLAIM OF PRIORITY

This application is a divisional of U.S. patent application Ser. No. 17/062,138, filed Oct. 2, 2020; which is a divisional of U.S. patent application Ser. No. 15/663,174, filed on Jul. 28, 2017, issued as U.S. Pat. No. 10,820,928 on Nov. 3, 2020; which claims the benefit of U.S. Provisional Patent Application No. 62/368,345, filed on Jul. 29, 2016, and claims the benefit of U.S. Provisional Patent Application No. 62/482,136, filed on Apr. 5, 2017; the benefit of priority of each of which is claimed hereby, and each of which are incorporated by reference herein in its entirety.

TECHNICAL FIELD

This document pertains generally, but not by way of limitation, to systems and methods for fixation of bones during orthopedic procedures. More particularly, this disclosure relates to, but not by way of limitation, vertebral bone anchors particularly suited for use in weakened or degenerative bone.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

Dynamic stabilization has also been used in spinal treatment procedures. Dynamic stabilization does not result in complete immobilization, but instead permits a degree of mobility of the spine while also providing sufficient support and stabilization to effect treatment. Dynamic stabilization systems can include a flexible construct extending between pedicle screws installed in adjacent vertebrae of the spine.

Examples of stabilization systems are the Dynesys® System, the Sequoia® Thoracolumbar Pedicle Screw System and the Lineum® OCT Spine System available from Zimmer Biomet Spine, Inc. of Broomfield, Colorado.

OVERVIEW

The present inventors have recognized, among other things, that a problem to be solved can include the need to provide bone anchors, such as threaded fasteners or screws, in bone that is degenerative or otherwise weakened. If bone anchors are inserted into weakened bone, there can be the potential for the fastener to move position or become dislodged, thereby rendering the anchoring effects provided by the fastener less effective or altogether ineffective.

The present subject matter can help provide a solution to various problems associated with the anchoring of fasteners in weakened or partially weakened bone by providing a sizing component that can be coupled to the fastener to enlarge the anchoring footprint of the fastener. The sizing component can be modular such that it can be attached to standard fasteners already typically maintained in inventory and/or can be combined with other sizing components to change the capabilities of the sizing component. Additionally, various sizing components can come in different shapes and configurations to accommodate bone that is weakened or degenerative in different capacities, thereby allowing a practitioner or surgeon the ability to choose from a variety of sizing components for use with particular bone defects of a particular patient. In various examples, the sizing component can be a sleeve into which a fastener is threaded to enlarge all or part of the shaft diameter of the fastener to provide radial anchoring in cancellous bone inside the bone, or a cap into which a fastener is threaded to provide axial anchoring into cortical bone at a surface of the bone.

In an example, the present subject matter can help provide a solution to this problem, such as by providing a bone anchor system comprising a fastener and a first sizing component. The fastener can comprise a shaft having a shaft diameter, an anchoring projection on the shaft, and a head at an end of the shaft. The bone screw system can have a variety of configurations, such as polyaxial, monoaxial, and uniaxial movement between the fastener and a housing. The first sizing component can be connected to the fastener. The first sizing component can comprise a first body portion having a first outer diameter larger than the shaft diameter, and a first bore extending through the first body portion, the first bore sized to receive the shaft diameter. The first sizing component can also include a first sizing located in the first bore to receive the anchoring projection on the shaft, a first outer surface at the first outer diameter, and a first circumferential bone engaging feature.

In another example, a bone anchor system can comprise a fastener, a first sizing component and a second sizing component. The fastener can comprise a threaded shaft configured to provide an anchoring footprint. The first sizing component can be configured to be connected to the threaded shaft. The first sizing component can include a first anchoring feature to increase a size of the anchoring footprint. The second sizing component can be configured to be connected to the threaded shaft. The second sizing component can include a second anchoring feature to increase the size of the anchoring footprint. The second anchoring feature can be different from the first anchoring feature.

In yet another example, a method of fastening a bone anchor can comprise forming a bore having a shaft diameter into a boney structure for a fastener shaft that is threaded, trialing the bore to determine bone integrity, selecting a sizing component based on the trialing, the sizing component having an enlarger diameter larger than the shaft diameter and a circumferential bone engaging feature, assembling the selected sizing component to the fastener shaft, and inserting the fastener shaft into the bore to engage the sizing component with the boney structure.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 3 is a perspective view of an exemplary bone anchor having a first embodiment of a sizing component comprising a threaded sleeve disposed along a shaft of a threaded fastener and having radial extending enlarging threading.

FIG. 4 is a perspective view of an exemplary bone anchor having a second embodiment of a sizing component comprising a cap disposed along a shaft of a threaded fastener and having axially extending fixation teeth.

DETAILED DESCRIPTION

Figures 1, 2:
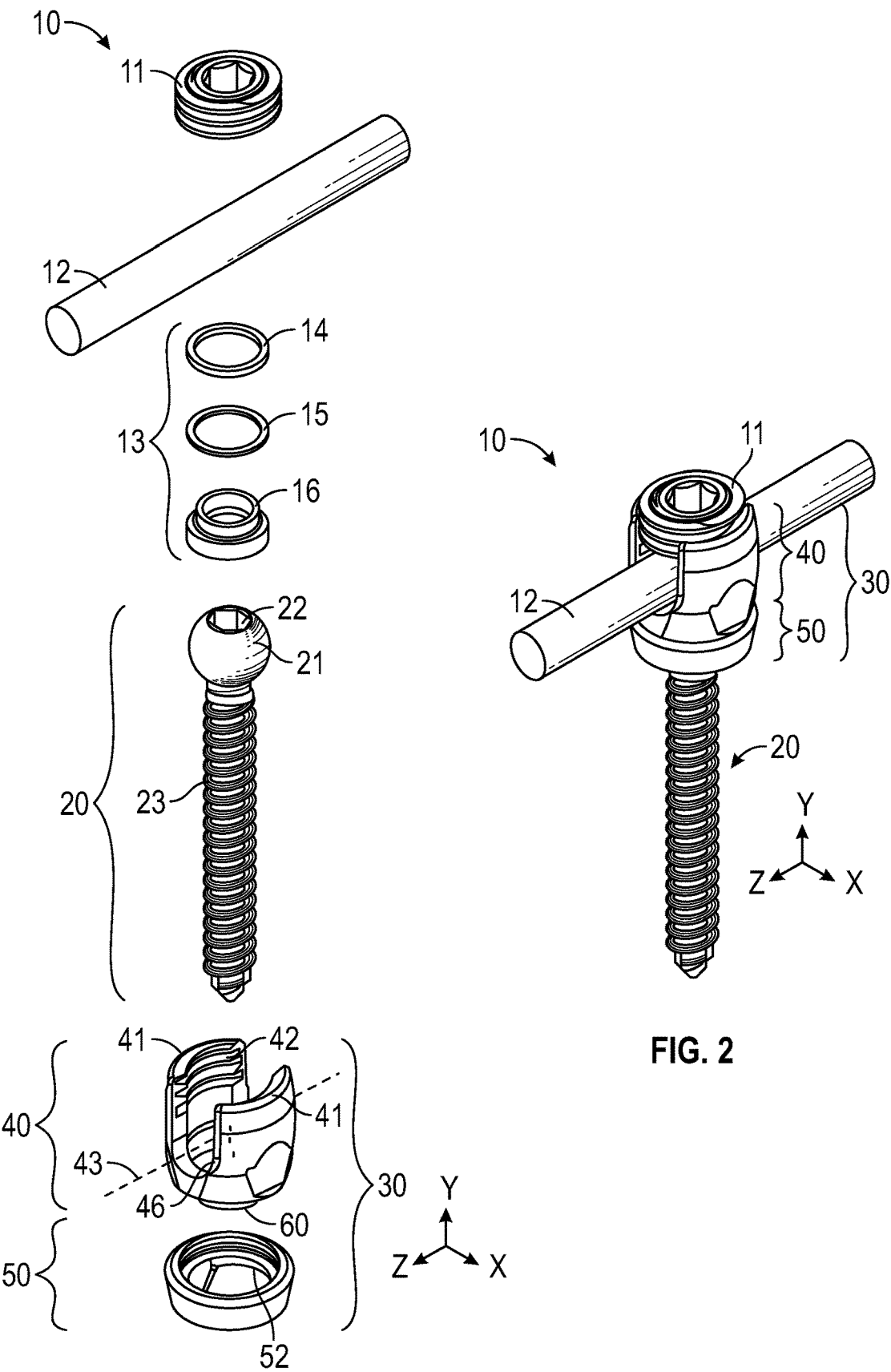
FIG. 1 is an exploded view of an exemplary bone anchor comprising a fastener, a housing, a rod and a closure member.
FIG. 2 is a perspective view of the bone anchor of FIG. 1 showing the rod secured to the housing between the fastener and the closure member.

FIG. 1 is an exploded view illustrating components of exemplary bone anchor 10 and rod 12. Bone anchor 10 can include closure member 11, retainer assembly 13, fastener 20 and housing 30. Retainer assembly 13 can include retainer ring 14, wave washer 15 and seat 16. Fastener 20 can include head 21, keyed portion 22 and shank 23. Housing 30 can include upper housing 40 and lower housing 50. Upper housing 40 can include opposing arms 41, threading 42 and U-shaped channel 43, which extends along a transverse axis that is transverse to the axial axis of fastener shank 23.

FIG. 2 is a perspective view of bone anchor 10 of FIG. 1 showing rod 12 secured to housing 30 between fastener 20 and closure member 11. FIGS. 1 and 2 are discussed concurrently.

Bone anchor 10 can be used to couple rod 12 or another elongate member to a boney structure. For example, shank 23 of fastener 20 can be inserted into and through upper housing 40 and lower housing 50 to connect to a pedicle of a vertebra. Retainer assembly 13 can be inserted into channel 43 to sit below rod 12. Retainer ring 14 can be connected to upper housing 40 to lock wave washer 15 and seat 16 in housing 30 below threading 42, thereby at least partially immobilizing fastener 20 within housing 30. Rod 12 can fit into U-shaped channel 43 formed by opposing arms 41, such as by being inserted into channel 43 from the top or proximal end of housing 30. Closure member 11, which can comprise a set screw or the like, can be threaded into threading 42 to push rod 12 down into channel 43 atop retainer assembly 13, thereby at least partially immobilizing rod 12 within bone anchor 10.

Bone anchor 10 can include particular degrees of adjustability that can help ensure that fastener 20 and elongate member 12 can be locked down at the particular locations and orientations desired by the practitioner or surgeon. For example, head 21 can be spherical in shape to allow rotation within housing 30. In particular, bone anchor 10 can allow for angular deviation of bone screw 20 away from the axial orientation shown in FIG. 1. Such an angular deviation may be referred to as "angulation", and desired angulations may exceed 35 degrees, 40 degrees, 45 degrees, or more, in some instances. Further description of such angulation is described in U.S. Pat. No. 9,289,244 to Hestad et al., which is hereby incorporated herein by this reference in its entirety.

Bone anchor 10 can be delivered or provided to or obtained by a practitioner in a semi-assembled state. In the exemplary design of FIG. 1, housing 30 can be modular, thus formed of multiple components coupled together. For example, housing 30 can include two components that are longitudinally adjacent to each other, namely upper housing 40 and lower housing 50. Thus, upper housing 40 and lower housing 50 can be pre-assembled. Also, fastener 20 can be pre-inserted into housing 30. Housing 30 can have a bore that extends longitudinally through the upper housing 40 and lower housing 50, generally coaxial with the longitudinal axis of bone anchor 10. Upper housing can include bore 46 and lower housing 50 can include bore 52 which can each be aligned and centered along the central axial axis of fastener 20 when fastener 20 is assembled with housing 30.

Fastener 20 can have threaded shank 23 that extends out from the bottom of lower housing 50 at bore 52 after passing through bore 46. Head 21 can be sized such that head 21 can pass into bore 46, but cannot pass through bore 52. Head 21 of fastener 20 can be generally spherical in shape, so that it may pivot with respect to housing 30 on lower housing 50.

Prior to final assembly, shank 23 can be dropped downward or otherwise inserted into the top of housing 30 through upper housing 40 and lower housing 50 so that head 21 can rest on lower housing 50. Alternatively, fastener 20 can be bottom-loaded into upper housing 40, and then lower housing 50 can be positioned around shank 23 and coupled onto upper housing 40, so that head 21 can be held in place within upper housing 40 atop lower housing 50.

Head 21 of fastener 20 can be held in place by retainer assembly 13, which can prevent fastener 20 from being pulled upward out of or otherwise displaced from housing 30. Retainer assembly 13 can allow pivoting of screw head 21 with respect to housing 30. Retainer assembly 13 can be typically in the form of one or more rings having a central aperture, which can allow the practitioner to insert a screwdriver through the apertures of the rings to engage a driver interface such as a keyed portion 22 on head 21 of fastener 20. The exemplary retainer assembly 13 in FIG. 1 can include seat 16 that can contact head 21, biasing member or wave washer 15, and retainer ring 14 farthest away from screw head 21. Seat 16 can include a concave annular region that has a radius of curvature matched to that of screw head 21, which facilitates pivoting of head 21. The concave annular region can also increase the frictional contact with head 21, which facilitates fastener 20 being held in place by seat 16 in the desired angular orientation.

Biasing member 15 can be inserted into channel 43 so as to be disposed on top of seat 16. Retainer ring 14 can be coupled to housing 30, such as via split-ring configuration, to secure biasing member 15 between seat 16 and retainer ring 14. In an example, biasing member 15 and retainer ring 14 can fit around an annular portion of seat 16. Next, rod 12 can be positioned on top of retainer ring 14.

To lock the components of bone anchor 10 in place, the practitioner can screw closure member 11 into threads 42 at the upper portion of housing 30 until closure member 11 engages rod 12. Closure member 11 can force rod 12 against the upper surface of seat 16, pushing retainer ring 14 and biasing member 15 down around seat 16, and in turn can force seat 16 against head 21 of the screw 20. Prior to final tightening of closure member 11, biasing member 15 can cause seat 16 to frictionally engage head 21 to resist movement of housing 30 with respect to fastener 20, which can allow for repositioning of shank 23. After complete tightening of closure member 11, the frictional force between seat 16 of retainer assembly 13 and head 21 can be sufficient to lock fastener 20 in place with respect to housing 30. In an example, U-shaped channel 43 can be deep enough so that closure member 11 does not force rod 12 against the bottom of U-shaped channel 43, with rod 12 being immobilized between seat 16 and closure member 11. In an example, retainer assembly 13 can be omitted, and closure member 11 can force rod 12 directly against head 21 of fastener 20 to secure fastener 20 in place. In an example, closure member 11 can push rod against portions of arms 41 forming the bottom of channel 43 to immobilize rod 12, with or without retainer assembly 14. In such an example with retainer assembly 14, angulation of fastener 20 can be partially immobilized by biasing member 15, and in such an example without retainer assembly 14 fastener 20 can be freely angulated (e.g. is not immobilized).

In practice, fastener 20 is threaded into bone that is structurally sound such that bone anchor 10 is substantially immobilized via engagement of threading on shank 23 extending radially from shank 23 into cancellous bone. However, sometimes bone at a location where it is desirable to provide anchoring by bone anchor 10 is inadequate for immobilizing a fastener. Such inadequate bone can arise from a variety of conditions, such as osteoporosis or other degenerative conditions that cause the bone structure to become compromised and weakened. Sometimes it is impractical to move bone anchor 10 to another location for a variety of reasons, such as there being no other available bone structure to provide anchoring or because a bore has already been drilled into the bone and it would unnecessarily further weaken the bone to drill another hole. The present disclosure addresses these issues in anchoring fasteners in boney structure by providing a sizing component that can be coupled to the fastener to increase the anchoring capacity or footprint of the fastener to reach a larger area and thereby reach healthy or otherwise structurally sound bone for anchoring.

FIG. 3 is a perspective view of exemplary bone anchor 60 having sizing component 62, which can comprise threaded sleeve 64, enlarging threading 66, first end 68, second end 70 and central bore 72. Bone anchor 60 can comprise fastener 74 and housing 76. Fastener 74 can include shaft 78, which can include anchor threading 80.

Bone anchor 60 can function similarly to that of bone anchor 10 of FIG. 1. For example, fastener 74 can include spherical head 82 that can rotate within housing 76, which can include slot 84 for receiving a rod. Sizing component 62 can be sized to mate with shaft 78 of fastener 74. For example, the outer diameter of shaft 78 can be sized to fit within the diameter of central bore 72, and internal female threading ("sizing threading") within central bore 72 can be sized to mate with male anchor threading 80. Sizing component 62, however, can be configured to operate with other bone anchor devices, such as bone anchor 200 of FIGS. 7-9.

Sleeve 64 can extend along a central axis that is configured to be co-axial with the central axis of shaft 78. Sleeve 64 can be tapered between first end 68 and second end 70 in order to provide a smooth transition between the outer diameter of shaft 78 and the outer diameter of sleeve 64. First end 68 of sleeve 64 can have a diameter of the desired outer diameter of sizing component 62. The diameter of first end 68 can be selected to increase the diameter of shaft 78 by any desirable amount to provide a larger anchoring footprint, as discussed below. Second end 70 can have a diameter that is just slightly larger than the outer diameter of shaft 78 sufficient to allow insertion of shaft 78 into sleeve 64. Thus, the diameter of sleeve 64 can increase from second end 70 to first end 68 so that, as shaft 78 is threaded into bone, sizing component 62 can be eased or gradually inserted into the bore in the bone. However, the diameter of sleeve 64 need not increase in a steady manner such that the widest portion of sleeve 64 need not be located at first end 68. Enlarging threading 66 on sleeve 64 can be sized to be the same as anchor threading 80 on shaft 78. For example, threading 66 on sleeve 64 can have the same pitch as threading 80 on shaft 78 to facilitate smooth entry of fastener 74 into a bone bore, particularly one that is pre-tapped with threading. In other words, anchor threading 80 and enlarging threading 66 can have the same pitch, but with different diameters, to ensure fastener 74 and sizing component 62 advance into the bone at the same rate and prevent binding. As such, threading 66 can comprise a continuation of threading 80 that in aggregate extends from tip 86, along shaft 78, onto second end 70, increasing in size along sleeve 64 and to first end 68. In other examples, threading 66 can be dual lead and threading 80 can be single lead with double pitch and have larger valleys to provide deep anchoring in the bone structure, as is discussed in greater detail with reference to FIG. 13.

Sizing component 62 can comprises sleeve 64 that can enlarge the diameter of shaft 78. Thus, as sleeve 64 is threaded onto shaft 78, the outer diameter of sleeve 64 and threading 66 can radially increase the diameter of bone anchor 60 to allow shaft 78 to increase or enlarge the anchoring footprint of fastener 74. In particular, shaft 78 can be configured to anchor bone anchor 60 into a bone bore having approximately the same diameter as shaft 78. However, as discussed, the boney structure may be weakened or deficient such that threads 80 cannot take adequate hold in the boney structure, thereby leaving open the possibility of bone anchor 60 becoming dislodged or displaced. Sleeve 64 can enlarge shaft 78 such that bone anchor 60 can become engaged in bone outside of, or larger than, the diameter of shaft 78. For example, sleeve 64 can be selected to have an outer diameter that is larger than a diseased or weakened bone area surrounding a bone bore into which shaft 78 is threaded. Thus, threading 66 of sleeve 64 can provide anchoring in healthy or structurally sound bone material.

Sleeve 64 can be threaded onto shaft 78 up to the proximal end of threading 80 near spherical head 82. As such, sleeve 64 can be configured to overcome deficient boney structure proximate a cortical bone surface surrounding the bone bore. Additionally, sleeve 64 can provide strengthening of shaft 78 near spherical head 82 in a location that can sometimes be subjected to stress during installation and use. The axial length of sleeve 64 allows sizing component 62 to engage healthy cancellous bone, displacing any weak or unhealthy cancellous bone. As discussed below, shaft 78 can be provided with a stop or locking feature (e.g. stop 248 of FIG. 11) to prevent sleeve 64 from backing out of the bone bore and protruding beyond the cortical bone.

The diameter of sleeve 64 can vary in different embodiments of sizing component 62. Likewise, the length of sizing component 62 between first end 68 and second end 79 can vary in different embodiments of sizing component 62. Thus, a variety of sizing components 62 can be provided in inventory, such as in a system, set, kit or package, or as part of a surgical system, to allow a surgeon or practitioner to intra-operatively select one or more sizing components of desired length and diameter, or material to compensate for or overcome weakened or defective boney structure at a particular surgical site of a patient at a location where the procedure is performed.

FIG. 4 is a perspective view of exemplary bone anchor 60 having sizing component 90, which can comprise cap 92 having axial fixation teeth 94 and central bore 96. Bone anchor 60 can be configured in the same manner as described with reference to FIG. 3 and can function similarly as bone anchor 10 of FIGS. 1 and 2. Bone anchor 60 can comprise fastener 74 and housing 76, which includes slot 84. Fastener 74 can include shaft 78, which can include threading 80, head 82 and tip 86.

Sizing component 90 can be sized to mate with shaft 78 of fastener 74. For example, the outer diameter of shaft 78 can be sized to fit within the diameter of central bore 96, and internal threading within central bore 96 can be sized to mate with threading 80. Sizing component 90, however, can be configured to operate with other bone anchor devices, such as bone anchor 200 of FIGS. 7-9.

Cap 92 can extend along a central axis that is configured to be co-axial with the central axis of shaft 78. Cap 92 can have an octagonal or hexagonal outer perimeter surface shape in order to engage a driver device. As such, insertion and removal of sizing component 90 can be facilitated with an instrument such as an open end wrench. However, the shape of the outer perimeter of cap 92 can have other configurations, such as square or circular.

Cap 92 can have an outer perimeter size selected to increase the diameter or size of shaft 78 any desirable amount to provide a larger anchoring footprint, as discussed below. In particular, fixation teeth 94 can extend from rim 98 to engage cortical bone surrounding shaft 78. Rim 98 can comprise a flange that can extend radially and/or axially from cap 92 to position fixation teeth 94 for engaging bone. Fixation teeth 94 can extend axially from rim 98 in a distal direction away from cap 92. Fixation teeth 94 can have a circumferential orientation to facilitate insertion into the cortical bone as sizing component 90 is rotated. In an example, fixation teeth 94 can be oriented in a clockwise circumferential direction when viewed from the proximal end of shaft 78 near spherical head 84 (as depicted in FIG. 4) to facilitate insertion of fixation teeth 94 when cap 92 is rotated in a clockwise or right-hand thread direction. In other examples, fixation teeth 94 can have different shapes or can be replaced with textured or jagged surfaces along rim 98 for engaging bone.

As cap 92 is threaded onto shaft 78, the outer size of cap 92 can radially increase the diameter of bone anchor 60 to allow shaft 78 to increase or enlarge the anchoring footprint of fastener 74. In particular, shaft 78 can be configured to anchor bone anchor 60 into a bone bore having approximately the same diameter as shaft 78. However, as discussed, the boney structure may be weakened or deficient such that threads 80 cannot take adequate hold in the boney structure, thereby leaving open the possibility of bone anchor 60 becoming dislodged or displaced. Cap 92 can enlarge shaft 78 such that bone anchor 60 can become engaged in bone outside of, or larger than, the diameter of shaft 78. For example, cap 92 can be selected to have an outer size that is larger than a diseased or weakened bone area surrounding a bone bore into which shaft 78 is threaded. Thus, fixation teeth 94 of cap 92 can provide anchoring in healthy or structurally sound bone material that surrounds the bone bore.

Cap 92 can be threaded onto shaft 78 up to the proximal end of threading 80 near spherical head 82. As such, cap 92 can be configured to overcome deficient boney structure proximate a cortical bone surface surrounding the bone bore. Shaft 78 continues to provide anchoring within the bone bore in cancellous bone. As discussed below, shaft 78 can be provided with a stop feature (e.g. stop 248 of FIG. 11) to prevent cap 92 from backing out from engagement with the cortical bone.

The diameter of cap 92 can vary in different embodiments of sizing component 90. Likewise, the shape, such as the length, of fixation teeth 94 can vary in different embodiments of sizing component 90. Thus, a variety of sizing components 90 can be provided in inventory, such as in a system, set, kit or package, or as part of a surgical system, to allow a surgeon or practitioner to intra-operatively select one or more sizing components of desired length and diameter to compensate for or overcome weakened or defective boney structure at a particular surgical site of a patient at a location where the procedure is performed.

Figure 5:
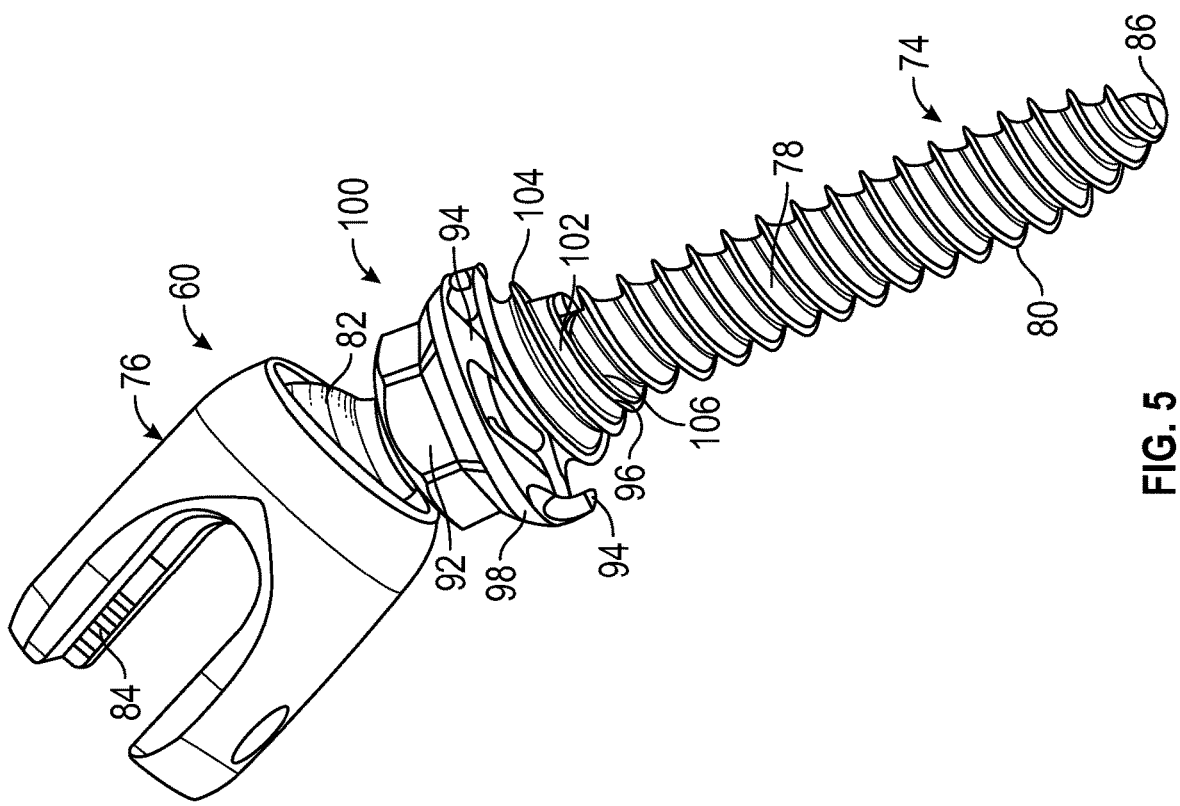
FIG. 5 is a perspective view of an exemplary bone anchor having a third embodiment of a sizing component comprising a cap having a threaded sleeve that extends along only a portion of a threaded fastener.

FIG. 5 is a perspective view of exemplary bone anchor 60 having sizing component 100, which can be configured similarly as sizing component 90 of FIG. 4 with the addition of extension sleeve 102. Sizing component 100 can also include cap 92, axial fixation teeth 94, central bore 96 and rim 98. Extension sleeve 102 can include threading 104. Bone anchor 60 can be configured in the same manner as described with reference to FIG. 3 and can function similarly as bone anchor 10 of FIGS. 1 and 2. Bone anchor 60 can comprise fastener 74 and housing 76, which includes slot 84. Fastener 74 can include shaft 78, which can include threading 80, head 82 and tip 86.

Cap 92 can function similarly as described with reference to FIG. 4. Extension sleeve 102 and threading 104 can function similarly as threaded sleeve 64 and threading 66 of sizing component 62 of FIG. 3. As such, FIG. 5 depicts a combination of the embodiments of FIGS. 3 and 4 wherein first end 68 of threaded sleeve 64 extends from cap 92.

Extension sleeve 102 can extend from cap 92 along a central axis that is configured to be co-axial with the central axis of shaft 78. Extension sleeve 102 can be tapered between cap 92 and distal end 106 in order to provide a smooth transition between the outer diameter of shaft 78 and the outer diameter of sleeve extension 102. The diameter of extension sleeve 102 can be selected to increase the diameter of shaft 78 any desirable amount to provide a larger anchoring footprint, as discussed herein. Distal end 106 can have a diameter that is just slightly larger than the outer diameter of shaft 78 sufficient to allow insertion of shaft 78 into extension sleeve 102. Thus, the diameter of extension sleeve 102 can be tapered so that, as shaft 78 is threaded into bone, sizing component 100 can be eased or gradually inserted into the bore in the boney structure. Threading 104 on extension sleeve 102 can be sized to be the same as threading 80 on shaft 78. For example, threading 104 on extension sleeve 102 can have the same pitch as threading 80 on shaft 78 to facilitate advancement into the boney structure at the same rate and prevent binding.

Sizing component 100 can comprises extension sleeve 102 that can be larger than the diameter of shaft 78, and cap 92 that can be larger than the diameter of extension sleeve 102. Thus, as sizing component 100 is threaded onto shaft 78, the outer diameter of extension sleeve 102 and threading 104 can effectively radially increase the diameter of shaft 78 to increase or enlarge the anchoring footprint of fastener 74, while cap 92 can further increase the size of the anchoring footprint. In particular, extension sleeve 102 can increase the anchoring footprint in the radial and axial directions to engage cancellous bone in a bone bore, while cap 92 and fixation teeth 94 can increase the anchoring footprint in the radial and axial directions to engage cortical bone. Thus, extension sleeve 102 can displace weak or unhealthy cancellous bone to engage healthy cancellous bone, while fixation teeth 94 can be extended radially beyond weak or unhealthy cortical bone to axially engage healthy cortical bone.

As discussed, the radial diameter of cap 92 and the axial length of teeth 94 can vary in different embodiments, and the radial diameter and axial length of extension sleeve 102 can vary in different embodiments such that different sizing components 100 can be used as components in different systems, sets, kits or packages. In the depicted example of FIG. 5, extension sleeve 102 has a length sized to only engage cancellous bone near the cortical surface of a bone bore. However, as shown in FIG. 6, extension sleeve 102 can be sized to extend along substantially all of shaft 78.

Figure 6:
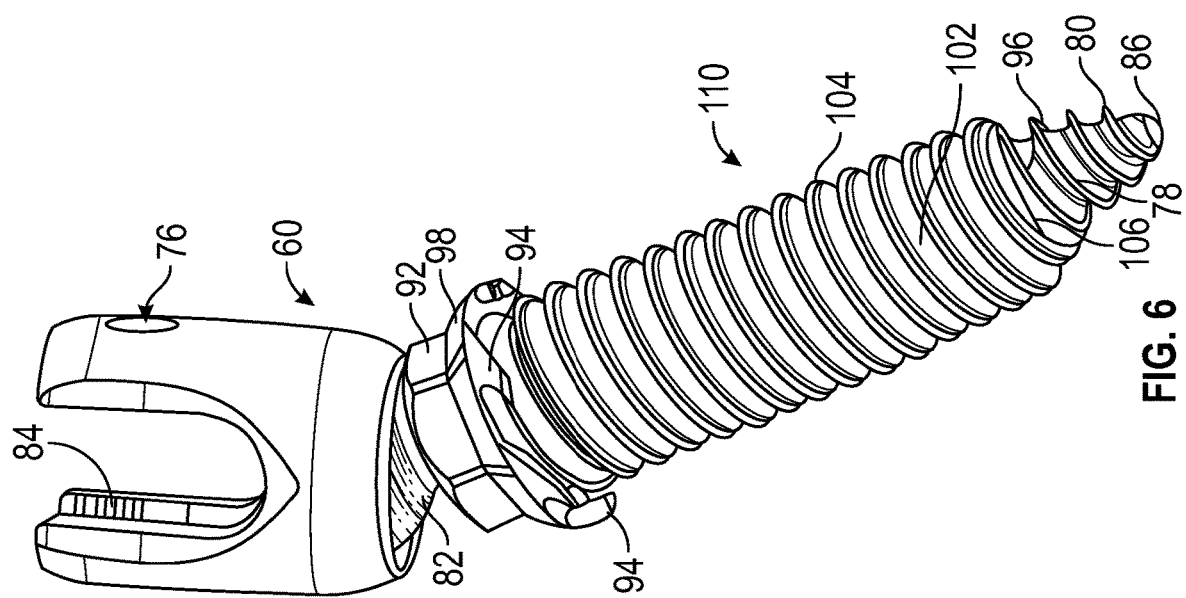
FIG. 6 is a perspective view of an exemplary bone anchor having a fourth embodiment of a sizing component comprising a cap having a threaded sleeve that extends along all but a tip portion of a threaded fastener.

FIG. 6 is a perspective view of exemplary bone anchor 60 having sizing component 110, which can be configured similarly as sizing component 100 of FIG. 4 with the addition of extension sleeve 102 having a greater length. Sizing component 110 can also include cap 92, axial fixation teeth 94, central bore 96 and rim 98. Extension sleeve 102 can include threading 104. Bone anchor 60 can be configured in the same manner as described with reference to FIG. 3 and can function similarly as bone anchor 10 of FIGS. 1 and 2. Bone anchor 60 can comprise fastener 74 and housing 76, which includes slot 84. Fastener 74 can include shaft 78, which can include threading 80, head 82 and tip 86.

As mentioned, sizing component 110 can be configured to operate in the same or a similar fashion as sizing component 100 of FIG. 5 except extension sleeve 102 is longer to engage a greater quantity of cancellous bone. Thus, distal end 106 can be positioned further down into a bone bore and the length of extension sleeve 102 can be used to displace a greater length of cancellous bone to allow threading 104 to engage a greater quantity of healthy cancellous bone. Sleeve 102 can extend across substantially all of shaft 78 except for the distal tapered end portion where tip 86 is located.

Figure 7:
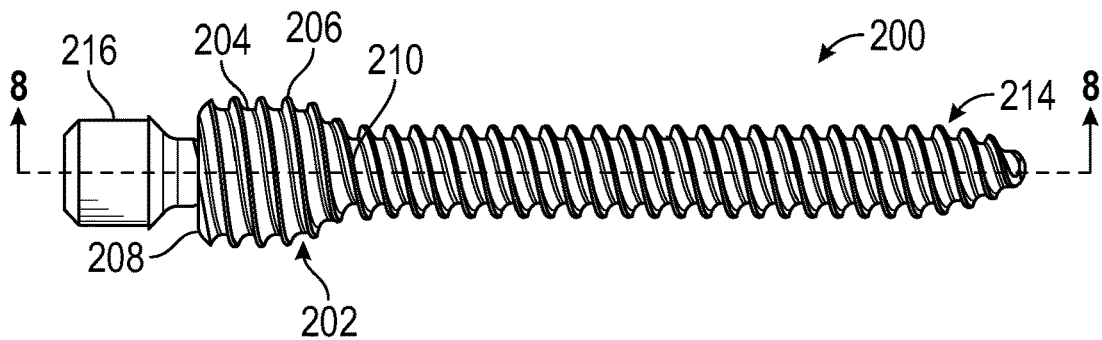
FIG. 7 is a side view of another exemplary bone anchor having a sizing component comprising a threaded sleeve.
Figure 8:
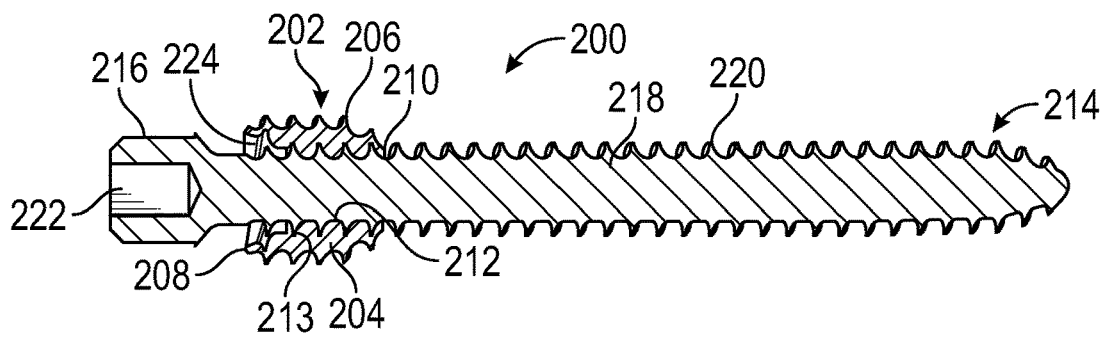
FIG. 8 is a cross-sectional view of the bone anchor and sizing component of FIG. 7.

FIG. 7 is a side view of exemplary bone anchor 200 having sizing component 202 comprising threaded sleeve 204. FIG. 8 is a cross-sectional view of bone anchor 200 and sizing component 202 of FIG. 7. FIGS. 7 and 8 are discussed concurrently. Threaded sleeve 204 can also comprise male anchor threading 206, first end 208, second end 210 and central bore 212 with female sizing threading 213. Bone anchor 200 can comprise fastener 214, which can include head 216, shaft 218, threading 220 and socket 222.

Bone anchor 200 can function similarly as bone anchor 10 of FIG. 1 and bone anchor 60 of FIG. 3, except bone anchor 200 includes head 216 instead of spherical head 82. As such, bone anchor 200 is not configured for use with housing 76 (FIG. 3). Instead, head 216 can be used with other components, such as plates, fusion systems, intra vertebral spacers and the like. Head 216 can be cylindrical for receding into another component. Head 216 can include socket 22 for receiving a drive tool, such as a screw driver or hex head wrench. In any event, fastener 214 can be used to secure bone anchor 200 to a boney structure.

Sizing component 202 can function similarly as sizing component 60 of FIG. 3. For example, sizing component 202 can have first end 208 and second end 210, with threaded sleeve 204 being tapered there-between to facilitate smooth insertion into bone. Threading 206 can be sized to match threading 220 of shaft 218 of fastener 214. In other words, threading 206 and threading 220 can have the same pitch to ensure fastener 214 and sizing component 202 advance into the boney structure at the same rate and prevent binding. Sleeve 204 can extend along a central axis that is configured to be co-axial with the central axis of shaft 218.

Sleeve 204 of sizing component 202 can enlarge the diameter of shaft 218 to radially increase the diameter of bone anchor 200 to allow shaft 218 to increase or enlarge the anchoring footprint of fastener 214. In particular, shaft 218 can be configured to anchor bone anchor 200 into a bone bore having approximately the same diameter as shaft 218. However, as discussed, the boney structure may be weakened or deficient such that threads 220 cannot take adequate hold in the boney structure, thereby leaving open the possibility of bone anchor 200 becoming dislodged or displaced. Sleeve 204 can enlarge shaft 218 such that bone anchor 200 can become engaged in bone outside of, or larger than, the diameter of shaft 218. For example, sleeve 204 can be selected to have an outer diameter that is larger than a diseased or weakened bone area surrounding a bone bore into which shaft 218 is threaded. Thus, threading 206 of sleeve 204 can provide anchoring in healthy or structurally sound bone material.

Sleeve 204 can be threaded onto shaft 218 up to the proximal end of threading 220 near head 216. As such, sleeve 204 can be configured to overcome deficient boney structure proximate a cortical bone surface surrounding the bone bore, and can be used to strengthen shaft 218. The axial length of sleeve 204 allows sizing component 202 to engage healthy cancellous bone, displacing any weak or unhealthy cancellous bone.

Figure 9:
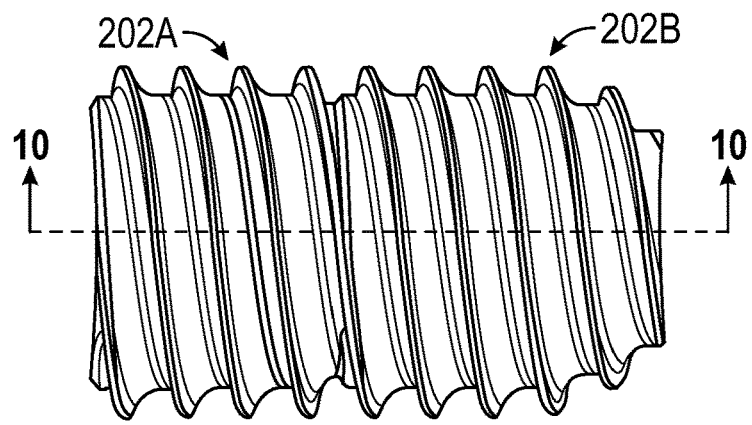
FIG. 9 is a side view of a first sizing component such as the one shown in FIGS. 7 and 8 axially abutted with a second sizing component of similar construction.
Figure 10:
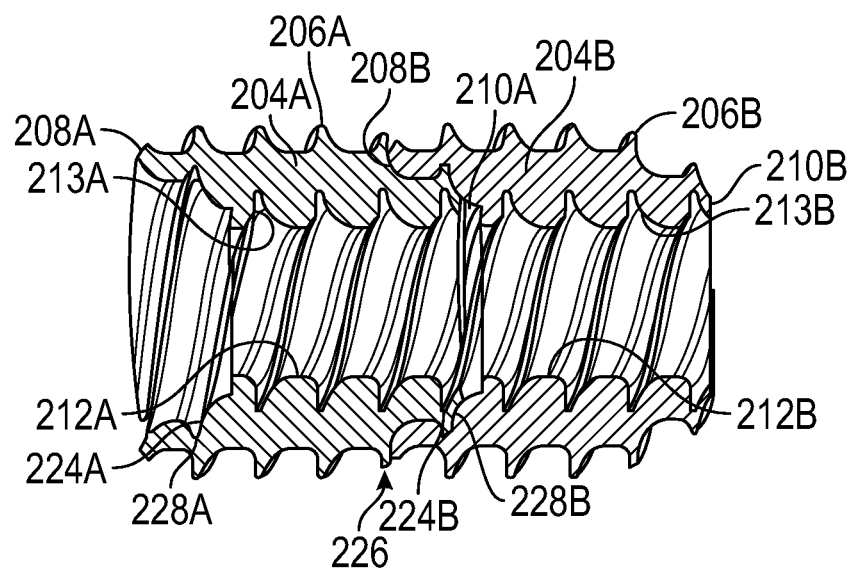
FIG. 10 is a cross-sectional view of the first and second sizing components of FIG. 9.

As with other examples and embodiments described herein, the sizes, e.g. length and diameter, of sleeve 204 can vary in different embodiments of sizing component 202 to permit a variety of sizing components 202 to be provided in inventory, such as in a system, set, kit or package, or as part of a surgical system, to allow a surgeon or practitioner to intra-operatively select one or more sizing components of desired length and diameter to compensate for or overcome weakened or defective boney structure at a particular surgical site of a patient at a location where the procedure is performed. However, first end 208 can include countersink or socket 224, which can allow for multiple sizing components 202 to be used in conjunction with each other to increase the axial anchoring footprint of sizing component 202, as shown in FIGS. 9 and 10. In other examples, socket 224 can be omitted from sizing component 202 to, for example, provide additional contact with the threaded fastener.

FIG. 9 is a side view of first sizing component 202A, such as sizing component 200 shown in FIGS. 7 and 8, axially abutted with second sizing component 202B of similar construction. FIG. 10 is a cross-sectional view of first and second sizing components 202A and 202B of FIG. 9. FIGS. 9 and 10 are discussed concurrently.

Sizing component 202A can include threaded sleeve 204A having threading 206A, first end 208A, second end 210A, central bore 212A, sizing threading 213A and socket 224A. Sizing component 202B can include threaded sleeve 204B having threading 206B, first end 208B, second end 210B, central bore 212B, sizing threading 213B and socket 224B.

As mentioned, second ends 210A and 210B can be tapered to provide smooth transitions with shaft 218 of fastener 214. Sockets 224A and 224B can be shaped in the mirror images of the tapers of second ends 210A and 210B to allow the tapering to be fully recessed into sockets 224A and 224B. For example, socket 224B can receive all or nearly all of the tapering of second end 210A such that there is no change in the diameter of the joined sizing components 202A and 202B between sleeves 204A and 204B at junction 226. Sockets 224A and 224B can include threading 228A and 228B, respectively to receive threading of a mating sizing component. For example, socket 224B of sizing component 202B can include threading 228B to receive threading 206A of sizing component 202A. Thus, multiple sizing components 202 can be axially stacked together to increase the effective length of the sizing component. This can reduce the number and variety of different sizing components needed in inventory to form different systems, sets, kits and packages as described herein.

Figure 11:
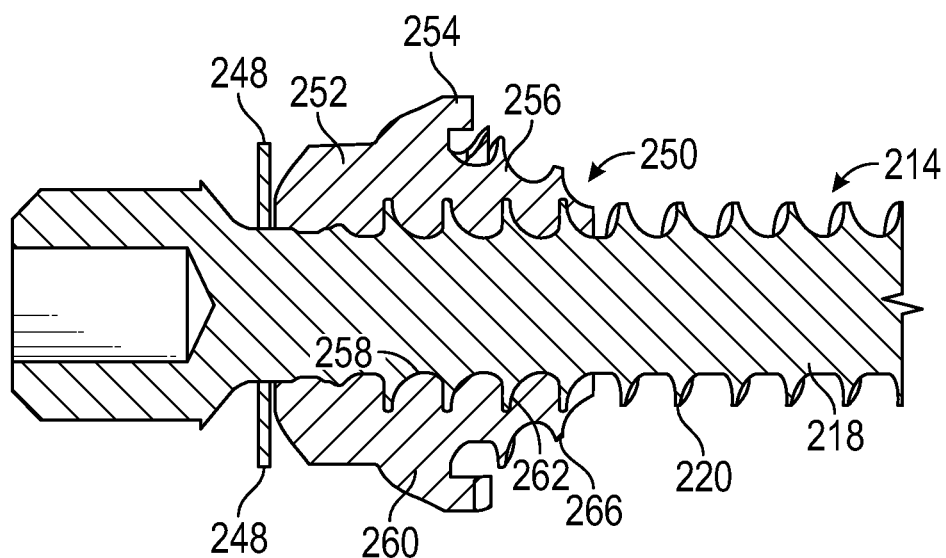
FIG. 11 is a cross-sectional view of a portion of the bone anchor of FIG. 8 having a stop and an embodiment of a sizing component having a cap with axial fixation teeth and a sleeve.

FIG. 11 is a cross-sectional view of a portion of fastener 214 of FIG. 8 having stop 248 and an exemplary sizing component 250 having cap 252 with axial fixation teeth 254 and sleeve 256. Sizing component 250 can also include central bore 258 and rim 260. Sizing component 250 is similar to sizing component 100 of FIG. 5, except being particularly sized for use with fastener 214. As such, central bore 258 can be sized to receive the diameter of shaft 218 of fastener 214, and central bore 258 can include female sizing threading 262 to receive male anchor threading 220 of shaft 218. However, as discussed, any of the sizing components described herein can have different dimensions in different embodiments for use with a variety of different fasteners and bone anchors.

Cap 252 can be shaped to have surfaces to engage a drive tool, such as a wrench or the like. Rim 260 can extend from cap 252 to position teeth 254 radially outward of sleeve 256. Rim 260 can extend radially outward from cap 252 and axially away from cap 252. Teeth 254 can extend axially from rim 260 to provide axial anchoring in bone surrounding fastener shaft 218. Sleeve 256 can extend axially from cap 252 within teeth 254. Sleeve 256 increases the diameter of shaft 218 such that threading 266 of sleeve 256 can increase the anchoring footprint of fastener 214 beyond what is provided by threading 220. Sleeve 256 and threading 266 can be shaped to smoothly mate with shaft 218 and threading 220. For example, sleeve 256 can be tapered to allow for a smooth entry of shaft 218 and sizing component 250 into a bone bore. Also, threading 266 can have the same pitch as threading 220 to allow for entry of shaft 218 and sizing component 250 into a bone bore without binding.

The various embodiments and examples of sizing components described herein can be made of a variety of different materials in different embodiments. In an example, the sizing components can be made of porous metal or biocompatible metal or alloys. In particular examples, the sizing components can be made from titanium or Trabecular Metal™, which is commercially available from Zimmer Inc. In other examples, the sizing components can be made of a polymer, such as polyether ether ketone (PEEK). In yet other examples, the sizing components can be made of autograft or allograft bone.

Figure 12:
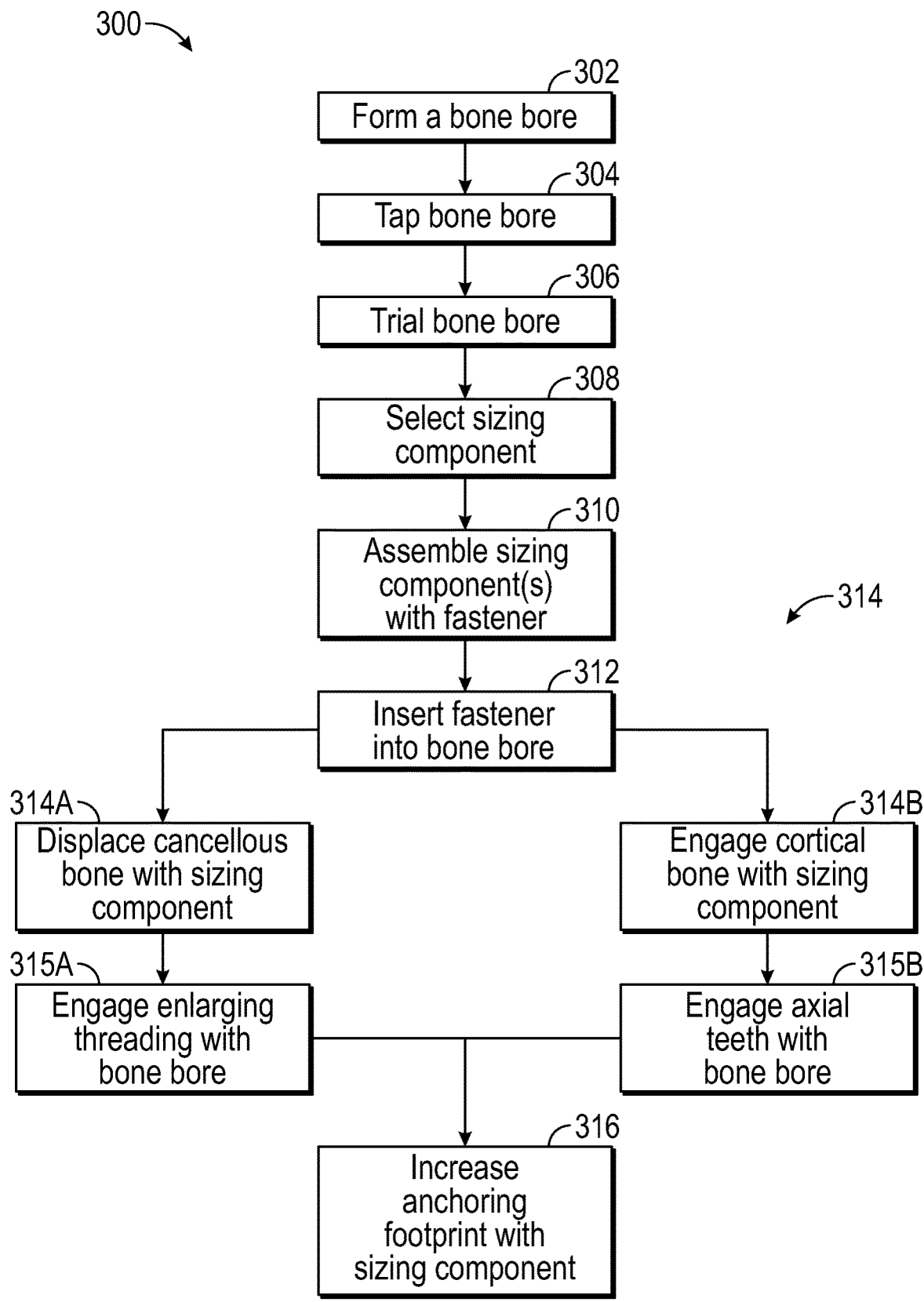
FIG. 12 is a flow chart diagramming a method of implanting a sizing component of the present application.

FIG. 12 is a flow chart diagramming method 300 of implanting a sizing component of the present application. Method 300 can include the steps of forming a bone bore in a boney structure 302, tapping the bone bore 304, trialing the bone bore 306, selecting a sizing component for use in the bone bore 308, assembling the sizing component with a fastener 310, inserting the fastener into the bone bore 312, engaging one or more portions of the sizing component with the boney structure 314 and increasing the anchoring footprint of the fastener with the sizing component 316.

Forming a bone bore at step 302 can comprise producing a bore or hole within a boney structure for receiving a bone anchor. A drill or an awl can be used to produce a channel through cortical bone and into cancellous bone. The bone bore can have a diameter that substantially matches the diameter of a fastener, such as a threaded fastener. As such, the diameter of the bone bore can be sized to accommodate threading of a fastener shaft.

Tapping the bone bore at step 304 can comprise using a thread tap to produce threading in the bone bore to match the threading of a desired threaded fastener of a bone anchor to be used in the bone bore. Any conventional thread tap can be used. In other examples, the bone bore may not be pre-threaded. As such, self-tapping bone fasteners can be used.

Trialing the bone bore at step 306 can comprise assessing the quality of bone at and around the bone bore via a variety of means. For example, the bone bore can be visually inspected by the surgeon or practitioner to assess the extent of damaged or unhealthy bone in and around the bone bore. Additionally, various instruments can be inserted into the bone bore to determine the extent of unhealthy or damaged bone. For example, a probe can be inserted into the bone bore to allow the surgeon or practitioner to feel the depth of any bone damage. Additionally, a bone anchor may be inserted into the bone bore to evaluate the effectiveness of a fastener used with the bone anchor. For example, a threaded fastener can be inserted or screwed into the bone bore and the surgeon or practitioner can tactilely feel if the fastener provides adequate anchoring support.

Selecting a sizing component at step 308 can comprise using information determined during trialing of the bone bore at step 306 to select one or more of the various sizing components described herein. For example, the radius of any damaged or unhealthy bone surrounding the bone bore can be used to select a sizing component of adequate diameter, and the depth of any damaged or unhealthy bone into the bone bore can be used to select a sizing component of adequate length.

Assembling the sizing component with the fastener at step 310 can comprise connecting the selected sizing component to the selected bone anchor. For example, a fastener of the selected bone anchor can be inserted or threaded into a sleeve or cap of a selected sizing component. In other examples, the sizing component can be connected to the fastener by other mechanisms. In yet other examples, the sizing component can be inserted into the bone first and the fastener can be passed through the sizing component second.

Inserting the fastener into the bone bore at step 312 can comprise threading the shaft of the fastener of the bone anchor into the bone bore. The shaft can be partially inserted into the bone bore before any sizing component engages boney structure of the bone bore. Alternatively, the sizing component can be initially threaded into the bone bore such that the fastener does not actually contact the bone bore.

The fastener can be advanced such that the sizing component engages the bone structure at step 314. The sizing component can engage the boney structure in a variety of different ways. In an example, the sizing component can be used to displace cancellous bone within the bone bore at step 314A, which can be accomplished by engaging enlarging threading of the sizing component, such as that disposed on a sleeve surrounding the shaft of the threaded fastener, with cancellous bone in the bone bore at step 315A. In an example, the sizing component can be used to engage cortical bone surrounding the bone bore at step 314B, which can be accomplished by engaging axially extending teeth of the sizing component, such as teeth that extend from a rim surrounding a cap surrounding the shaft of the threaded fastener, to engage cortical bone surrounding the bone bore at step 315B. Additionally, sizing components can be configured to engage both cortical and cancellous bone such that steps 315A and 315B can be achieved concurrently (or in quick succession as the fastener with the sizing component is advanced into the bone). As a result of step 314, the anchoring footprint of the bone anchor can be increased with the sizing component(s) at step 316. As such, the bone anchor can be more securely held in place in the bone bore with a reduced risk of becoming displaced.

Figure 13:
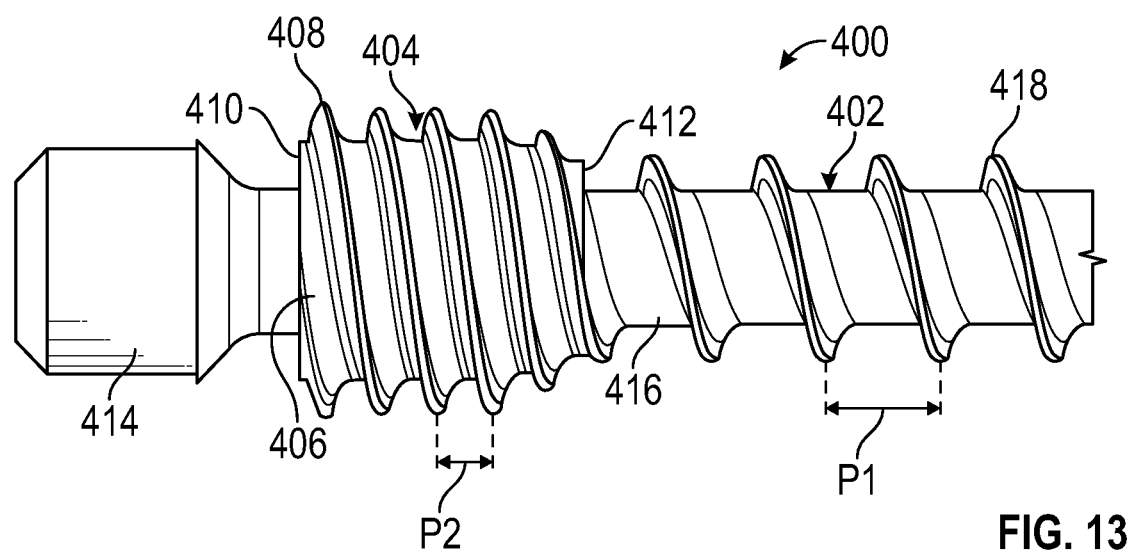
FIG. 13 is a side view of another exemplary bone anchor including a fastener having a first external thread pitch and a sizing component having a second external thread pitch.

FIG. 13 is a side view of exemplary bone anchor 400 including fastener 402 having first external thread pitch P1 and sizing component 404 having second external thread pitch P2. Sizing component 404 can comprise threaded sleeve 406 having threading 408 extending between first end 410 and second end 412 of threaded sleeve 406. Fastener 402 can comprise head 414 and shaft 416. Shaft 416 can include threading 418 that extends between a tip (not shown) and head 414.

Bone anchor 400 can operate similarly to bone anchor 200 of FIG. 7 with the exception that threading 418 can be at a different pitch than threading 220. In particular, threading 408 can be dual lead and threading 418 can be single lead with double pitch. Threading 418 can be configured to have large, deep valleys and can be widely-spaced between threading to provide for deep anchoring in cancellous bone structure. Threading 408 can be configured to have small, shallow valleys and can be closely-spaced to provide abundant anchoring in cortical bone. In one example, pitch P1 can be approximately 3.0 mm and pitch P2 can be approximately 1.5 mm.

Various Notes & Examples

Example 1 can include or use subject matter such as a bone fastener system that can comprise: a fastener and a first sizing component. The fastener can comprise: a shaft having a shaft diameter; an anchoring projection on the shaft; and a head at an end of the shaft. The first sizing component can be connected to the fastener. The first sizing component can comprise: a first body portion having a first outer diameter larger than the shaft diameter; a first bore extending through the first body portion, the first bore sized to receive the shaft diameter; a first sizing located in the first bore to receive the anchoring projection on the shaft; a first outer surface at the first outer diameter; and a first circumferential bone engaging feature extending from the first outer surface.

Example 2 can include, or can optionally be combined with the subject matter of Example 1, to optionally include an anchoring projection that can comprise threading and the first sizing comprises mating threading.

Example 3 can include, or can optionally be combined with the subject matter of one or any combination of Examples 1 or 2 to optionally include a first circumferential bone engaging feature that can comprise first enlarging threading on the first outer surface.

Example 4 can include, or can optionally be combined with the subject matter of one or any combination of Examples 1 through 3 to optionally include a pitch of the first enlarging threading that can match a pitch of the threading on the shaft.

Example 5 can include, or can optionally be combined with the subject matter of one or any combination of Examples 1 through 4 to optionally include a second sizing component that can comprise a second body portion having a second outer diameter larger than the shaft diameter, a second bore extending through the second body portion, and mating threading located in the second bore to receive the threading on the shaft.

Example 6 can include, or can optionally be combined with the subject matter of one or any combination of Examples 1 through 5 to optionally include a second outer diameter that can be approximately equal to the first outer diameter.

Example 7 can include, or can optionally be combined with the subject matter of one or any combination of Examples 1 through 6 to optionally include a first sizing component that can include a tapered distal tip, and a second sizing component that can include a countersunk proximal end, wherein the tapered distal tip fits into the countersunk proximal end.

Example 8 can include, or can optionally be combined with the subject matter of one or any combination of Examples 1 through 7 to optionally include a shaft that can further comprise a tapered end portion opposite the head, the shaft can extend over a first length from the head to the tapered end portion, and a first body portion that can have a second length approximately equal to the first length.

Example 9 can include, or can optionally be combined with the subject matter of one or any combination of Examples 1 through 8 to optionally include a first circumferential bone engaging feature that can comprise axially extending teeth.

Example 10 can include, or can optionally be combined with the subject matter of one or any combination of Examples 1 through 9 to optionally include a first body portion that can further include a radially extending flange connected to the first outer surface and from which the axially extending teeth extend.

Example 11 can include, or can optionally be combined with the subject matter of one or any combination of Examples 1 through 10 to optionally include axially extending teeth that can be circumferentially oriented.

Example 12 can include, or can optionally be combined with the subject matter of one or any combination of Examples 1 through 11 to optionally include tool-engaging surfaces located on the first body portion on an opposite side of the radially extending flange as the axially extending teeth.

Example 13 can include, or can optionally be combined with the subject matter of one or any combination of Examples 1 through 12 to optionally include first enlarging threading on the first outer surface.

Example 14 can include, or can optionally be combined with the subject matter of one or any combination of Examples 1 through 13 to optionally include a stop located along the shaft to abut the first body portion.

Example 15 can include or use subject matter such as a bone anchor system that can comprise: a fastener, a first sizing component and a second sizing component. The fastener can comprise a threaded shaft configured to provide an anchoring footprint. The first sizing component can be configured to be connected to the threaded shaft, the first sizing component can include a first anchoring feature to increase a size of the anchoring footprint. The second sizing component can be configured to be connected to the shaft, the second sizing component can include a second anchoring feature to increase the size of the anchoring footprint, the second anchoring feature being different from the first anchoring feature.

Example 16 can include, or can optionally be combined with the subject matter of Example 15, to optionally include a first anchoring feature that can comprise a sleeve that radially expands a diameter of the threaded shaft.

Example 17 can include, or can optionally be combined with the subject matter of one or any combination of Examples 15 or 16 to optionally include a second anchoring feature that can expand the diameter of the threaded shaft a greater amount than the first anchoring feature.

Example 18 can include, or can optionally be combined with the subject matter of one or any combination of Examples 15 through 17 to optionally include a second anchoring feature that can have a second length greater than a first length of the first anchoring feature.

Example 19 can include, or can optionally be combined with the subject matter of one or any combination of Examples 15 through 18 to optionally include a second anchoring feature that can comprise axially extending teeth.

Example 20 can include or use subject matter such as a method of fastening a bone anchor, the method can comprise: forming a bore having a shaft diameter into a boney structure for a fastener shaft; trialing the bore to determine bone integrity; selecting a sizing component based on the trialing, the sizing component having a diameter larger than the shaft diameter and a circumferential bone engaging feature; assembling the selected sizing component to the fastener shaft; and inserting the fastener shaft into the bore to engage the sizing component with the boney structure.

Example 21 can include, or can optionally be combined with the subject matter of Example 20, to optionally include a circumferential bone engaging feature comprising external threading, and threading the fastener shaft into the bore to engage the external threading of the sizing component with cancellous bone in the bore in the boney structure.

Example 22 can include, or can optionally be combined with the subject matter of Examples 20 or 21, to optionally include a circumferential bone engaging feature that comprises axially extending teeth, and threading the fastener shaft into the bore to engage the axially extending teeth of the sizing component with cortical bone of the boney structure surrounding the bore.

Example 23 can include, or can optionally be combined with the subject matter of one or any combination of Examples 20 through 22 to optionally include tapping the bore to form threading that mates with the fastener shaft.

Example 24 can include, or can optionally be combined with the subject matter of one or any combination of Examples 20 through 23 to optionally include assembling the sizing component with the fastener shaft until the sizing component engages a stop feature.

Example 25 can include, or can optionally be combined with the subject matter of one or any combination of Examples 20 through 24 to optionally include engaging two or more sizing components together along the fastener shaft.

Example 26 can include, or can optionally be combined with the subject matter of one or any combination of Examples 20 through 25 to optionally include trialing the bore comprises probing the bore to determine an extent of weakened bone adjacent the bore; and selecting the sizing component comprises determining a size of the sizing component to compensate for the extent of the weakened bone.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with The claimed invention is:

1. A bone anchor system, comprising:
   a fastener comprising a threaded shaft at a distal end of the fastener, the threaded shaft having a shaft diameter and configured to provide a first anchoring footprint of a first size;
   a bone engaging component operable to receive the fastener within a bore extending through a body portion, the bore extending through the body portion including internal threading that is configured to engage with external threading on the threaded shaft, the bone engaging component including a bone engaging feature extending from the body portion, wherein the bone engaging feature and the body portion are configured to provide a second anchoring footprint that is greater in size than the first anchoring footprint; and
   a housing including a channel, the channel positioned at a proximal end of the bone anchor system relative to the threaded shaft, wherein the channel is operable to receive an elongate member.

2. The bone anchor system of claim 1, wherein the bone engaging feature comprises a plurality of teeth that axially extend relative to the body portion.

3. The bone anchor system of claim 2, further comprising engaging surfaces located on the body portion on an opposite side of the body portion as the plurality of teeth.

4. The bone anchor system of claim 1, wherein the channel extends along a channel axis that is transverse to a shaft axis through the threaded shaft.

5. The bone anchor system of claim 4, wherein the channel is positioned directly above the threaded shaft such that the channel axis is located directly above the shaft axis.

6. The bone anchor system of claim 1, wherein the channel is defined by opposing arms of the housing.

7. The bone anchor system of claim 1, further comprising a threaded component positioned exterior to the threaded shaft and distal of the housing.

8. The bone anchor system of claim 6, wherein the housing includes an upper housing and a lower housing, wherein the opposing arms are portions of the upper housing.

9. The bone anchor system of claim 8, wherein the fastener passes through the lower housing, and wherein the upper housing includes a bore through which a head of the fastener is accessible.

10. A bone anchor system comprising:
    a fastener comprising:
      a shaft having a shaft diameter, wherein the shaft has threading; and
      a head at an end of the shaft; and
    a bone engaging component operable to receive the fastener, the bone engaging component comprising:
      a body portion having an outer diameter larger than the shaft diameter;
      a bore extending through the body portion, the bore sized to receive the shaft diameter such that the body portion is immovable from an angle defined with respect to a longitudinal axis through a length of the shaft when the shaft is inserted into the bore;
      an outer surface at the outer diameter; and
      a bone engaging feature extending from the outer surface;
    a housing including a channel, the channel positioned at a proximal end of the bone anchor system and operable to receive an elongate member; and
    a threaded component positioned exterior to the shaft and distal of the housing.

11. The bone anchor system of claim 10, wherein the bone engaging feature comprises a plurality of teeth that axially extend relative to the body portion.

12. The bone anchor system of claim 11, wherein the body portion further includes a radially extending flange connected to the outer surface and from which the plurality of teeth axially extend.

13. The bone anchor system of claim 12, further comprising engaging surfaces located on the body portion on an opposite side of the radially extending flange as the plurality of teeth.

14. The bone anchor system of claim 10, wherein the channel extends along a channel axis that is transverse to a shaft axis through the shaft.

15. The bone anchor system of claim 14, wherein the channel is positioned directly above the shaft such that the channel axis is located directly above the shaft axis.

16. The bone anchor system of claim 10, wherein the channel is defined by opposing arms of the housing.

17. The bone anchor system of claim 16, wherein the housing includes an upper housing and a lower housing, wherein the opposing arms are portions of the upper housing.

18. The bone anchor system of claim 17, wherein the fastener passes through the lower housing, and wherein the upper housing includes a bore through which the head of the fastener is accessible.

19. A method of engaging a bone anchor system with a boney structure, the method comprising:
    forming a bone aperture into the boney structure for a fastener including a head and a threaded shaft having a shaft diameter;
    selecting a bone engaging component, the bone engaging component having a body portion and a bone engaging feature, the body portion having a diameter larger than the shaft diameter;
    inserting the threaded shaft within the bone engaging component to form the bone anchor system;
    threading the threaded shaft into the bone engaging component to cause the bone-engaging feature to engage with the boney structure such that the bone engaging component is fixedly coupled to the threaded shaft at an angle defined with respect to a longitudinal axis through the threaded shaft; and
    positioning an elongate member within a channel within a housing at a proximal end of the bone anchor system relative to the threaded shaft, wherein the bone anchor system further comprises a threaded component positioned exterior to the threaded shaft and distal of the housing.

* * * * *